United States Patent [19]

Algieri

[11] Patent Number: 4,772,704

[45] Date of Patent: Sep. 20, 1988

[54] 2,5-DISUBSTITUTED-4(3H)-PYRIMIDONES HAVING HISTAMINE H$_2$-RECEPTOR ANTAGONIST ACTIVITY

[75] Inventor: Aldo A. Algieri, Fayetteville, N.Y.

[73] Assignee: Bristol-Myers Company, New York, N.Y.

[21] Appl. No.: 534,426

[22] Filed: Sep. 21, 1983

[51] Int. Cl.$^4$ .......................................... C07D 239/46
[52] U.S. Cl. ................................... 544/320; 544/295; 544/296; 544/321
[58] Field of Search ...................... 544/320, 321, 296; 424/251; 514/255, 272

[56] References Cited

U.S. PATENT DOCUMENTS 4,241,056 12/1980 Wetzel et al. ...................... 514/150

FOREIGN PATENT DOCUMENTS

| 3677 | 8/1979 | European Pat. Off. . |
| 4793 | 10/1979 | European Pat. Off. . |
| 15138 | 9/1980 | European Pat. Off. . |
| 24873 | 3/1981 | European Pat. Off. . |
| 49173 | 6/1982 | European Pat. Off. . |
| 3025226 | 1/1981 | Netherlands . |
| 2933142 | 4/1981 | Netherlands . |

OTHER PUBLICATIONS

Ganellin et al, Federation Proceedings, 35, 1924 (1976).
Ganellin, Drugs of the Future, 1, 13 (1976).
Nagatsu et al, Chem. Abst. 95:220082e.
Wetzel, Bernd et al, Chem. Abst. 95:97788k.

Primary Examiner—Donald G. Daus
Assistant Examiner—Cecilia Shen
Attorney, Agent, or Firm—Aldo A. Algieri

[57] ABSTRACT

Histamine H$_2$-antagonists of the formula:

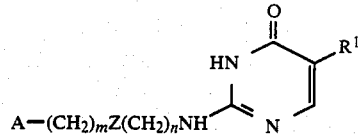

wherein
m is an integer of from zero to 2, inclusive;
n is an integer of from 2 to 5 inclusive;
Z is sulfur, oxygen or methylene;
R$^1$ is NO$_2$ or NR$^2$R$^3$;
R$^2$ and R$^3$ each are independently hydrogen or (lower)alkyl, or, when R$^2$ is hydrogen, R$^3$ also may be formyl, carboalkoxy, alkanoyl or benzoyl;
A is phenyl, furyl, thienyl, pyridyl, thiazolyl, imidazolyl, oxazolyl, oxadiazolyl, thiadiazolyl, triazolyl, isoxazolyl, isothiazolyl, pyrimidinyl, pyrazolyl, pyridazinyl or pyrazinyl; provided that A contains one or two substituents, the first substituent being selected from $$-(CH_2)_qN=C\begin{matrix}NHR^4\\ \\ NH_2\end{matrix} \quad \text{and} \quad -(CH_2)_qNR^6R^7$$

and the second substituent being selected from (lower)alkyl, hydroxy, trifluoromethyl, halogen, amino, hydroxymethyl and (lower)alkoxy;
q is an integer of from 0 to 6, inclusive;
R$^4$ is a hydrogen atom, a (lower)alkyl group optionally substituted by one or more halogen atoms, provided that there is no halogen atom on the carbon atom attached to the nitrogen atom, or a cyclo(lower)alkyl, cyclo(lower)alkyl(lower)alkyl, (lower)alkanoyl or benzoyl group;
R$^6$ and R$^7$ each are independently hydrogen, (lower)alkyl, (lower)alkenyl, (lower)alkynyl, phenyl(lower)alkyl or (lower)alkoxy(lower)alkyl in which the (lower)alkoxy moiety is at least two carbon atoms removed from the nitrogen atom, or R$^6$ and R$^7$, taken together with the nitrogen atom to which they are attached, may be pyrrolidino, methylpyrrolidino, dimethylpyrrolidino, morpholino, thiomorpholino, piperidino, methylpiperidino, dimethylpiperidino, hydroxypiperidino, N-methylpiperazino, homopiperidino, heptamethyleneimino, octamethyleneimino or 3-azabicyclo[3.2.2]non-3-yl; or a nontoxic pharmaceutically acceptable acid addition salt thereof.

16 Claims, No Drawings

2,5-DISUBSTITUTED-4(3H)-PYRIMIDONES HAVING HISTAMINE H$_2$-RECEPTOR ANTAGONIST ACTIVITY

SUMMARY OF THE INVENTION

Certain 2,5-disubstituted-4(3H)-pyrimidones having the formula:

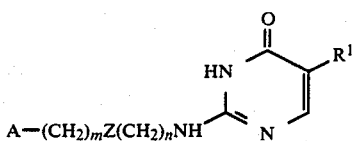

wherein A, m, Z, n and R$^1$ are as defined below, and their nontoxic pharmaceutically acceptable salts, are potent histamine H$_2$-receptor antagonists which inhibit gastric acid secretion and are useful in the treatment of peptic ulcers and other pathological hypersecretory conditions.

BACKGROUND AND PRIOR ART

Burimamide (IIa) was the first clinically effective histamine H$_2$-receptor antagonist. It inhibits gastric secretion in animals, including man, but oral absorption is poor.

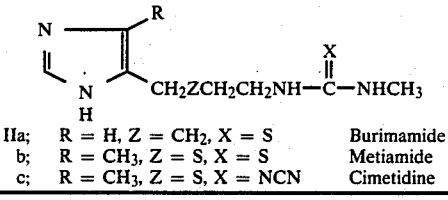

| | | |
|---|---|---|
| IIa; | R = H, Z = CH$_2$, X = S | Burimamide |
| b; | R = CH$_3$, Z = S, X = S | Metiamide |
| c; | R = CH$_3$, Z = S, X = NCN | Cimetidine |

Metiamide (IIb), a subsequently evaluated histamine H$_2$-antagonist, is more potent than burimamide and is orally active in man. Clinical utility was limited, however, owing to toxicity (agranulocytosis). Cimetidine (IIc) is as effective an histamine H$_2$-antagonist as metiamide, without producing agranulocytosis, and has recently been marketed as an anti-ulcer drug.

Reviews on the development of histamine H$_2$-antagonists, including those discussed in the preceding paragraph, may be found in C. R. Ganellin, et al, *Federation Proceedings*, 35, 1924 (1976), in *Drugs of the Future*, 1, 13 (1976) and in references cited therein.

A large number of 2,5-disubstituted pyrimidone histamine H$_2$-receptor antagonists having the general formula:

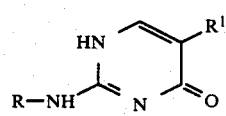

are known in the art. Thus, European Patent Application No. 4,793, published Oct. 17, 1979,; European Patent Application No. 3,677, published Aug. 22, 1979; European Patent Application No. 15,138, published Sept. 3, 1980; European Patent Application No. 24,873, published Mar. 11, 1981; European Patent Application No. 49,173, published Apr. 7, 1982; and World Patent Application No. 8,000,966, published May 15, 1980 disclose such compounds wherein R can be a group similar to the group substituted on the 2-amino group of the compounds disclosed and claimed herein and R$^1$ can be hydrogen, alkyl or substituted alkyl. However, none of these applications disclose such compounds substituted at the 5-position with a nitro group or an amino group as is the case with the compounds disclosed and claimed herein.

COMPLETE DESCRIPTION

This application relates to histamine H$_2$-antagonists which are effective inhibitors of gastric acid secretion in animals, including man, which are useful in the treatment of peptic ulcers and other conditions caused or exacerbated by gastric acidity, and which have the formula:

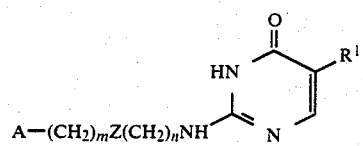

wherein
m is an integer of from zero to 2, inclusive;
n is an integer of from 2 to 5 inclusive;
Z is sulfur, oxygen or methylene;
R$^1$ is NO$_2$ or NR$^2$R$^3$;
R$^2$ and R$^3$ each are independently hydrogen or (lower)alkyl, or, when R$^2$ is hydrogen, R$^3$ also may be formyl, carboalkoxy, alkanoyl or benzoyl;
A is phenyl, furyl, thienyl, pyridyl, thiazolyl, imidazolyl, oxazolyl, oxadiazolyl, thiadiazolyl, triazolyl, isoxazolyl, isothiazolyl, pyrimidinyl, pyrazolyl, pyridazinyl or pyrazinyl; provided that A contains one or two substituents, the first substituent being selected from

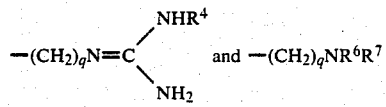

and the second substituent being selected from (lower)alkyl, hydroxy, trifluoromethyl, halogen, amino, hydroxymethyl and (lower)alkoxy;
q is an integer of from 0 to 6, inclusive;
R$^4$ is a hydrogen atom, a (lower)alkyl group optionally substituted by one or more halogen atoms, provided that there is no halogen atom on the carbon atom attached to the nitrogen atom, or a cyclo(lower)alkyl, cyclo(lower)alkyl(lower)alkyl, (lower)alkanoyl or benzoyl group;
R$^6$ and R$^7$ each are independently hydrogen, (lower)alkyl, (lower)alkenyl, (lower)alkynyl, phenyl(lower)alkyl or (lower)alkoxy(lower)alkyl in which the (lower)alkoxy moiety is at least two carbon atoms removed from the nitrogen atom, or R$^6$ and R$^7$, taken together with the nitrogen atom to which they are attached, may be pyrrolidino, methylpyrrolidino, dimethylpyrrolidino, morpholino, thiomorpholino, piperidino, methylpiperidino, dimethylpiperidino, hydroxypiperidino, N-methylpiperazino, homopiperidino, heptamethyleneimino, octamethyleneimino or 3-azabicyclo[3.2.2]non-3-yl; or a nontoxic pharmaceutically acceptable acid addition salt thereof.

This invention also relates to processes for the preparation of the compounds of Formula I and to intermediates useful in the preparation of the compounds of Formula I.

The present invention includes within its scope all possible tautomeric forms, geometric isomers, optical isomers and zwitterionic forms of the compounds of Formula I, as well as mixtures thereof. Although the compounds of Formula I are shown as 4-pyrimidones, those skilled in the art will appreciate that they, as well as the intermediates for preparing them, may also exist as the tautomeric 4-hydroxypyrimidines, e.g.,

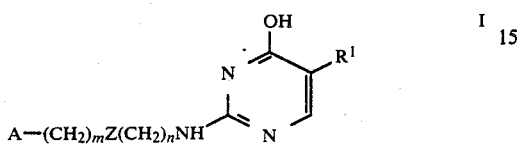

As used herein and in the claims, the term "lower" when used in conjuction with the terms "(lower)alkyl", "(lower)alkoxy", "(lower)alkanoyl", "(lower)alkenyl", "(lower)alkynyl", "phenyl(lower)alkyl" and "(lower)alkoxy(lower)alkyl" means straight or branched chain groups containing from 1 to 6 carbon atoms. Preferably these groups contain from 1 to 4 carbon atoms and, most preferably, they contain 1 to 2 carbon atoms. The term "nontoxic pharmaceutically acceptable salts" is intended to include salts of the compounds of Formula I with any nontoxic pharmaceutically acceptable acid. Such acids are well-known and include hydrochloric, hydrobromic, sulfuric, sulfamic, phosphoric, nitric, maleic, fumaric, succinic, oxalic, benzoic, methanesulfonic, tartaric, citric, camphorsulfonic, levulinic and the like. The salts are made by methods known in the art.

In the compounds of Formula I, $R^1$ is preferably $NO_2$, $NH_2$, $NHCO_2C_2H_5$, or NHCHO. Substituent A preferably is piperidinomethylphenyl, dimethylaminomethylthienyl, piperidinomethylthienyl, or dimethylaminomethylfuryl. Substituent $R^4$ preferably is hydrogen, (lower)alkyl or 2,2,-trifluoroethyl. Substituent Z preferably is sulfur or oxygen. It is preferred that m is zero or 1 and n is 2 or 3.

As presently envisaged, the most preferred compounds of Formula 1 are:
(1) 5-carbethoxyamino-2-[3-(3-piperidinomethylphenoxy)propylamino]-4(3H)-pyrimidone;
(2) 5-amino-2-[3-(3-piperidinomethylphenoxy)propylamino]-4(3H)-pyrimidone;
(3) 5-nitro-2-[3-(3-piperidinomethylphenoxy)propylamino]-4(3H)-pyrimidone;
(4) 5-nitro-2-{2-[(5-dimethylaminomethyl-3-thienyl)methylthio]ethylamino}-4(3H)-pyrimidone;
(5) 5-nitro-2-{2-[(5-piperidinomethyl-3-thienyl)methylthio]ethylamino}-4(3H)-pyrimidone;
(6) 2-{2-[(5-dimethylaminomethyl-2-furyl)methylthio]ethylamino}-5-nitro-4(3H)-pyrimidone;
(7) 5-amino-2-{2-[(5-dimethylaminomethyl-3-thienyl)methylthio]ethylamino}-4(3H)-pyrimidone;
(8) 5-amino-2-{2-[(5-piperidinomethyl-3-thienyl)methylthio]ethylamino}-4(3H)-pyrimidone;
(9) 5-amino-2-{2-[(5-dimethylaminomethyl-2-furyl)methylthio]ethylamino}-4(3H)-pyrimidone; and
(10) 5-formamido-2-[3-(3-piperidinomethylphenoxy)propylamino]-4(3H)-pyrimidone;
and their nontoxic, pharmaceutically acceptable acid addition salts.

The compounds of Formula I may be prepared by various reaction schemes.

REACTION SCHEME 1

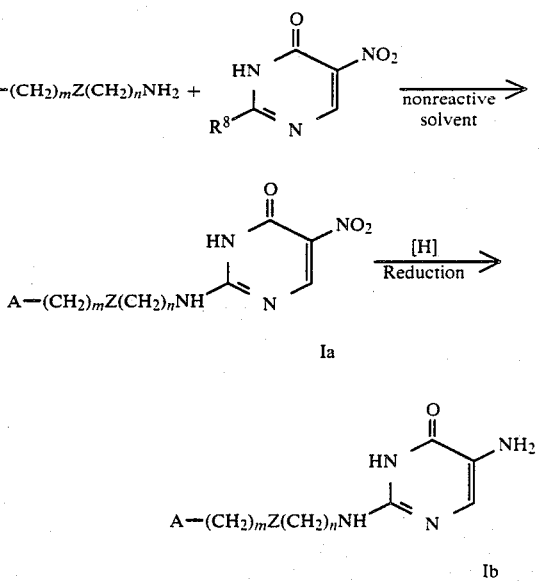

in which $R^8$ is a good leaving group such as fluoro, chloro, bromo, iodo, alkylthio, nitroamino, phenoxy, substituted phenoxy, alkoxy or the like. Suitable leaving groups are well known in the art. The reactions are conducted in an inert solvent such as methanol or ethanol. It is preferred to conduct the initial reaction by heating the reactants at reflux. Reduction may be carried out with hydrogen gas in the presence of a suitable catalyst such as Raney nickel or a reducing catalyst such as sodium dithionite.

REACTION SCHEME 2

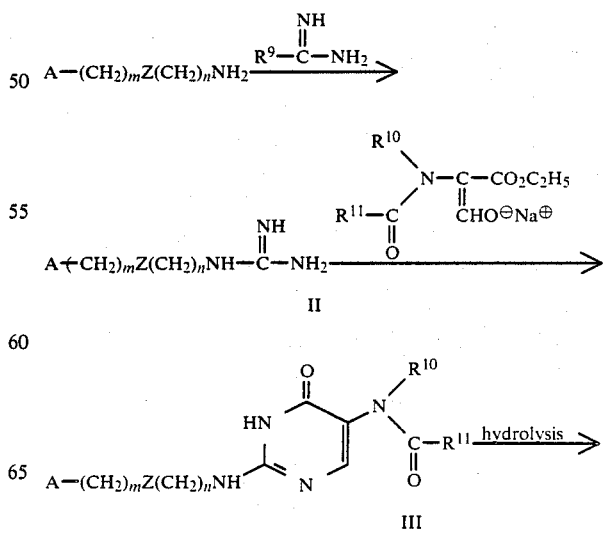

-continued

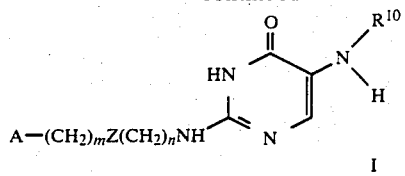

I wherein $R^9$ is thioalkoxy or

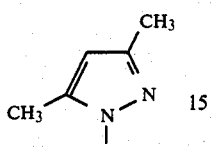

$R^{10}$ is H or lower alkyl, and $R^{11}$ is lower alkyl, aryl, alkoxy or aryloxy. The reactions are conducted in an inert solvent such as methanol or ethanol. It is preferred to conduct the initial reaction to obtain a compound of Formula II by heating the reactants at reflux; and to conduct the second reaction to obtain a compound of Formula III at from room temperature up to the reflux temperature of the solvent.

REACTION SCHEME 3

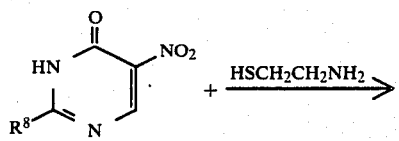

-continued

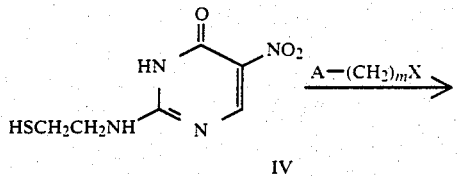

IV

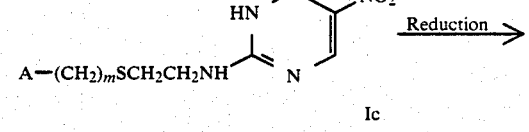

Ic

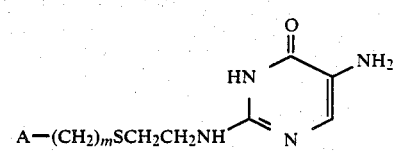

Id wherein $R^8$ is the same as previously defined and X is a conventional leaving group or hydroxy. Suitable leaving groups "X" for use in this reaction are well-known to those skilled in the art. They include, for example, fluoro, chloro, bromo, iodo, —$O_3SR^{12}$ wherein $R^{12}$ is (lower)alkyl [e.g., methanesulfonate], —$O_3SR^{13}$ wherein $R^{13}$ is aryl or substituted aryl [e.g., benzenesulfonate, p-bromobenzenesulfonate or p-toluenesulfonate], —$O_3SF$, acetoxy and 2,4-dinitrophenoxy. The first reaction to obtain a compound of Formula IV is conducted in an inert solvent at a temperature ranging between room temperature and the reflux temperature of the solvent; and the second reaction to obtain a compound of Formula Ic is conducted in an inert solvent preferably containing about one equivalent base. When X is hydroxy and m is equal to 1, the reaction is conducted in an acidic medium.

REACTION SCHEME 4

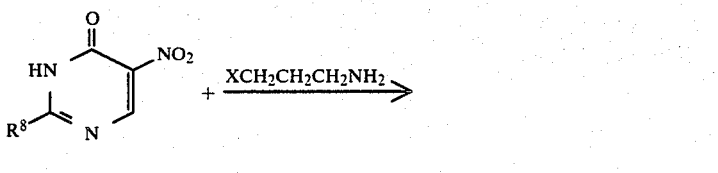

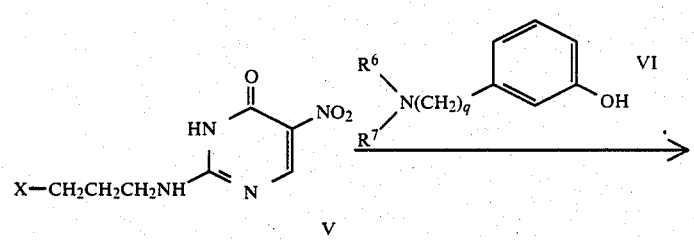

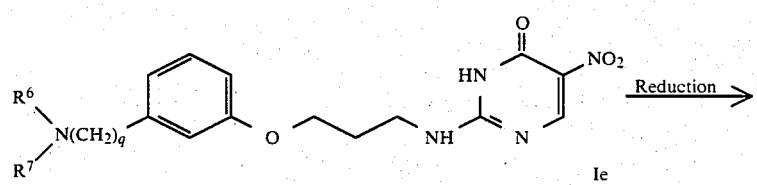

-continued

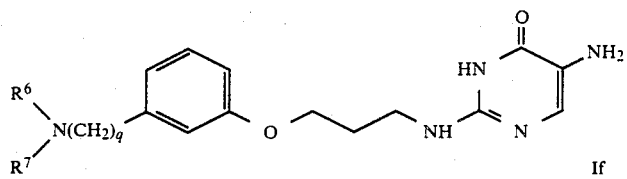

If wherein q, $R^6$, $R^7$ and $R^8$ are the same as previously defined and X is a conventional leaving group as described previously, or hydroxy. When X is hydroxy in compound V, it is converted to a conventional leaving group by reaction with an activating agent such as thienyl chloride, toluene sulfonic acid or the like. The reaction is conducted in an inert solvent at from room temperature to the reflux temperature of the solvent. Compound V is reacted with compound VI in an inert solvent, preferably in the presence of about one equivalent of base, more preferably in the presence of a phase transfer catalyst such as tetrabutylammonium hydroxide.

For therapeutic use, the pharmacologically active compounds of Formula I will normally be administered as a pharmaceutical composition comprising as the (or an) essential active ingredient at least one such compound in its basic form or in the form of a nontoxic pharmaceutically acceptable acid addition salt, in association with a pharmaceutically acceptable carrier.

The pharmaceutical compositions may be administered orally, parenterally or by rectal suppository. A wide variety of pharmaceutical forms may be employed. Thus, if a solid carrier is used, the preparation may be tableted, placed in a hard gelatin capsule in powder or pellet form, or in the form of a troche or lozenge. If a liquid carrier is employed, the preparation may be in the form of a syrup, emulsion, soft gelatin capsule, sterile solution for injection, or an aqueous or non-aqueous liquid suspension. The pharmaceutical compositions are prepared by conventional techniques appropriate to the desired preparation.

The dosage of the compounds of this invention will depend not only on such factors as the weight of the patient, but also on the degree of gastric acid inhibition desired and the potency of the particular compound being utilized. The decision as to the particular dosage to be employed (and the number of times to be administered per day) is within the discretion of the physician, and may be varied by titration of the dosage to the particular circumstances of the specific patient. With the preferred compounds of this invention, each oral dosage unit will contain the active ingredient in an amount of from about 2 mg to about 300 mg, and most preferably from about 4 mg to about 100 mg. The active ingredient will preferably be administered in equal doses from one to four times a day.

Histamine $H_2$-receptor antagonists have been shown to be effective inhibitors of gastric secretion in animals and man, Brimblecombe et al, *J. Int. Med. Res.*, 3, 86 (1975). Clinical evaluation of the histamine $H_2$-receptor antagonist cimetidine has shown it to be an effective therapeutic agent in the treatment of peptic ulcer disease, Gray et al, *Lancet*, 1, 8001 (1977). One of the preferred compounds of this invention has been compared with cimetidine in various tests and has been found to be more potent that cimetidine as a histamine $H_2$-receptor antagonist as shown in Tables 1 and 2.

Determination of Gastric Antisecretory Activity in the Gastric Fistula Rat

Male Long Evans rats weighing about 240–260 grams at the time of cannula implantation are used. The design and implantation of the stainless steel cannula into the anterior wall of the fore-stomach are carried out essentially as described by Pare et al, *Laboratory Animal Science*, 27, 244 (1977). The fistula components are designed and the operative procedure is carried out exactly as described in the above reference. Post operatively the animals are individually housed in solid bottom cages with sawdust and are allowed food and water ad libitum throughout the entire recovery period. Animals are not used for test purposes for at least 15 days after the operative procedure.

The animals are fasted but allowed water ad libitum for 20 hours before the testing procedure is to begin. Immediately prior to collection, the cannula is opened and the stomach washed gently with 30–40 ml of warm saline or distilled water to remove any residual contents. The catheter is then screwed into the cannula in place of the plugging screw and the rat is placed in a clear plastic rectangular cage measuring 40 cm long, 15 cm wide and 13 cm high. The bottom of the cage has a slit approximately 1.5 cm wide and 25 cm long running down the center to accommodate the catheter which hangs through it. In this way, the rat is not restricted and can move freely about the cage during collection periods. The remainder of the assay is carried out as described by Ridley et al, *Research Comm. Chem. Path. Pharm.*, 17, 365 (1977).

Gastric secretions collected during the first hour after washing the stomach are discarded as they may be contaminated. For oral evaluation, the catheter is then removed from the cannula and replaced with the plugging screw. Water (2 ml/kg) is administered orally via gastric intubation and the animal is returned to the cage for 45 minutes. After this time the plugging screw is removed and replaced with a catheter to which a small plastic vial has been attached to collect the gastric secretions. A two-hour sample is collected (this represents the control secretion), the catheter is removed and replaced with the plugging screw. The test drug is now administered orally in a volume of 2 ml/kg via gastric intubation. Forty-five minutes later the plugging screw is again removed, replaced with the catheter attached to a small plastic vial and another 2-hour sample is collected. The secretions in the second sample are compared to those of the control sample in order to determine the effects of the test drug.

When test compounds are to be evaluated parenterally, the animal is injected ip or sc with the test compound vehicle in a volume of 2 ml/kg immediately after discarding the initial 60-minute collection. A two-hour sample is collected (control secretion) and the animals are injected either ip or sc with the test compound in a volume of 2 ml/kg. An additional two-hour sample is collected and its secretions are compared to those of the control period to determine drug effects.

The samples are centrifuged and placed in a graduated centrifuge tube for volume determination. Titratable acidity is measured by titrating a one-ml sample to pH 7.0 with 0.02N NaOH, using an Autoburet and an electrometric pH meter (Radiometer). Titratable acid output is calculated in microequivalents by multiplying the volume in milliliters by the acid concentration in milliequivalents per liter.

Results are expressed as percent inhibition relative to control readings. Dose response curves are constructed and $ED_{50}$ values are calculated by regression analyses. At least three rats are used at each dosage level and a minimum of three dosage levels are utilized for determination of a dose response curve.

TABLE 1

| | Gastric Antisecretory Activity In The Gastric Fistula Rat | |
|---|---|---|
| Compound | $ED_{50}$ sc µmoles/kg | Potency Ratio (cimetidine = 1.0) |
| cimetidine | 3.48 (2.3–5.5)* | 1.0 |
| Example 2 | 0.15 (0.08–0.2)* | 26 (13–50)* |

*95% confidence limits.

Determination of Gastric Antisecretory Activity In The Heidenhain Pouch Dog

Prior to surgery, hematology and blood chemistry profiles are obtained and an assessment made as to the general health of selected female dogs. Dogs are vaccinated with Tissue Vax 5 (DHLP—Pitman-Moore) and housed in general animal quarters for four weeks' observation so incipient diseases may become apparent. Dogs are fasted with water ad libitum 24 hours prior to surgery.

Anesthesia is induced with Sodium Pentothal (Abbott) 25–30 mg/kg iv. Subsequent anesthesia is maintained with methoxyflurane (Pitman-Moore). A midline linea alba incision from xiphoid to umbilicus provides good exposure and ease of closure. The stomach is pulled up into the operative field, the greater curvature stretched out at multiple points and clamps placed along the selected line of incision. The pouch is made from the corpus of the stomach so that true parietal cell juice is obtained. About 30% of the corpus volume is resected. The cannula is made of light-weight, biologically-inert material such as nylon or Delrin with dimensions and attachments after DeVito and Harkins (J. Appl. Physiol., 14, 138 (1959). Post operatively, dogs are medicated with antibiotics and an analgesic. They are allowed 2–3 months for recovery. Experiments are carried out in the following way: Dogs are fasted overnight ($\approx$18 hours) with water ad libitum prior to each experiment. The dogs are placed in a sling and a saphenous vein cannulated for drug administration. Histamine as the base (100 µg/kg/hr) and chlorpheniramine maleate (0.25 mg/kg/hr) are infused continuously (in a volume of 6 ml/hr) with a Harvard infusion pump.

Ninety minutes' infusion are allowed for the dogs to reach a steady state of acid output. At this time the drug or normal saline (control) is administered concomitantly with the secretagogue in a volume of 0.5 ml/kg over a 30 second period. When oral studies are to be carried out, the drug is administered via gastric gavage in a volume of 5 ml/kg. Infusion of the secretagogue is continued and 15 minute samples of the gastric juice are taken for 4.5 hours. Each sample is measured to the nearest 0.5 ml and titratable acidity is determined by titrating a 1 ml sample to pH 7.0 with 0.2N NaOH, using an Autoburet and an electrometric pH meter (Radiometer). Titratable acid output is calculated in microequivalents by multiplying the volume in milliliters by the acid concentration in milliequivalents per liter.

Results are expressed as percent inhibition relative to control readings and the response is the average for five dogs at that dose level.

TABLE 2

| | Gastric Antisecretory Activity In The Heidenhain Pouch Dog | | |
|---|---|---|---|
| Compound | Dose* [µmoles/kg] | % Maximum Inhibition | Potency Ratio [cimetidine = 1.0] |
| (Intravenous) | | | |
| Cimetidine | 6.0 | 94 | 1.0 |
| Compound of Example 2 | 0.094 | 90 | 50 |
| (Oral) | | | |
| Cimetidine | 12.0 | 95 | 1.0 |
| Compound of Example 2 | 0.5 | 86 | 20 |

*single dose was used in 5 dogs for compound of Example 2

In addition to the results shown in Table 2, the antisecretory activity of the compound of Example 2 in both the intravenous and oral dog models shows a prolonged duration of action relative to cimetidine.

EXAMPLE 1

5-Carbethoxyamino-2-[3-(3-piperidinomethylphenoxy)-propylamino]-4(3H)-pyrimidone A. N-[3-(3-Piperidinomethylphenoxy)propyl]guanidine nitrate A solution of 3-(3-piperidinomethylphenoxy)propylamine obtained from the dihydrochloride (7.45 g; 30.0 mmoles) and 3,5-dimethylpyrazole-1-carboxamidine nitrate (6.04 g; 30.0 mmoles) in 100 ml of absolute ethanol was heated at reflux temperature for 1 hour, then kept at room temperature for 16 hours. The reaction mixture was concentrated under reduced pressure and the residue was triturated with ether, filtered and dried to give 9.82 g of the title compound, mp 74°–76° C.

B. 5-Carbethoxyamino-2-[3-(3-piperidinomethylphenoxy)propylamino]-4(3H)-pyrimidone A mixture of 3-(3-piperidinomethylphenoxy)propylguanidine nitrate (10.5 g; 29.71 mmoles) [prepared in Step A], and the sodium salt of ethyl carbethoxyaminoformylacetate (6.69 g; 29.8 mmoles) in 57 ml of methanol was treated with 57% sodium hydride dispersion (1.25 g; 29.8 mmoles). The resulting mixture was heated at an oil bath temperature of 60° C. for 16 hours. The reaction mixture was evaporated under reduced pressure and the residue taken up with acetonitrile. The turbid solution was filtered, washed with n-pentane and evaporated to give crude product. The semi-solid product was placed on 250 g of silica gel (230–400 mesh) and chromatographed by flash chromatography using gradient elution of methanolmethylene chloride containing 1% NH$_4$OH. The appropriate fractions were combined, evaporated and the solid residue recrystallized from acetonitrile to give the title compound, mp 171°–173° C.

Anal. Calc'd for $C_{22}H_{31}N_5O_4$: C, 61.52; H, 7.28; N, 16.31. Found: C, 61.13; H, 7.27; N, 16.24.

EXAMPLE 2

5-Amino-2-[3-(3-piperidinomethylphenoxy)-propylamino]-4(3H)-pyrimidone

A suspension of 5-carbethoxyamino-2-[3-(3-piperidinomethylphenoxy)propylamino]-4(3H)-pyrimidone (1.70 g; 3.96 mmoles) in 11.3 ml (28.3 meq.) of 10% aqueous NaOH was heated at an oil bath temperature of 120° C. for 20 minutes. The reaction mixture was neutralized with acetic acid and evaporated under reduced pressure. The residue was placed on 250 g of silica gel (230–400 mesh) and chromatographed by flash chromatography using $CH_2Cl_2/CH_3OH/NH_4OH$ (80:20:1) as the eluent. The appropriate fractions containing product were combined, evaporated and treated wih ethanolic hydrochloric acid, and then diluted with ether to give 0.28 g of the title compound as its hydrochloride salt. The NMR spectrum (100 MHz) in $d_6$ dimethyl sulfoxide gave the following resonances δ: 7.14 (m, 4H); 6.94 (s, 1H); 4.0 (m, 4H); 3.32 (t, 2H); 2.84 (m, 4H); 1.94 (m, 2H); 1.66 (m, 6H).

Anal. Calc'd for $C_{19}H_{27}N_5O_2.HCl$: C, 57.93; H, 7.16; N, 17.78; Cl, 9.00. Found (corr. for 2.37% $H_2O$): C, 56.67; H, 7.27; N, 15.60; Cl, 8.87.

EXAMPLE 3

5-Nitro-2-[3-(3-piperidinomethylphenoxy)-propylamino]-4(3H)-pyrimidone

A solution of 3-(3-piperidinomethylphenoxy)propylamine (8.20 g; 33.0 mmoles) and 2-methylthio-5-nitro-4-hydroxypyrimidine (6.20 g; 32.5 mmoles) [prepared according to the procedure described in U.S. Pat. No. 4,241,056] in 35 ml of ethanol was stirred at reflux temperature for 18 hours. The reaction mixture was evaporated under reduced pressure, and the residue was placed on 250 g of silica gel (230–400 mesh) and chromatographed by flash chromatography using a gradient elution of methanol-methylene chloride. The appropriate fractions were combined and evaporated, and the product was recrystallized from tetrahydrofuran to give the title compound, mp 161°–164° C.

The NMR spectrum (90 MHz) in $d_6$ dimethyl sulfoxide shows the presence of approximately 0.25 moles of tetrahydrofuran.

Anal. Calc'd for $C_{19}H_{28}N_5O_4.0.25C_4H_8O$: C, 59.19; H, 6.71; N, 17.27. Found (corr. for 0.19% $H_2O$): C, 59.22; H, 6.70; N, 17.54.

EXAMPLE 4

5-Amino-2-[3-(3-piperidinomethylphenoxy)-propylamino]-4(3H)-pyrimidone

A suspension of 5-nitro-2-[3-(3-piperidinomethylphenoxy)propylamino]-4(3H)-pyrimidone (0.50 g; 1.29 mmoles) and a catalytic amount of Raney nickel (approximately 0.7 cm$^3$) in 50 ml of methanol was hydrogenated in a Parr apparatus at 50 psi for 2.75 hours. The reaction mixture was filtered and evaporated, and the residue was placed on 90 g of silica gel (230–400 mesh) and chromatographed by flash chromatography using a gradient elution of methanol-methylene chloride containing 1% $NH_4OH$. The appropriate fractions were combined and evaporated, and the semi-solid product was acidified with methanolic hydrochloric acid and precipitated with ether to give the title compound as a dihydrochloride salt, mp 182°–184° C.

Anal. Calc'd for $C_{19}H_{27}N_5O_2.2HCl$: C, 50.87; H, 6.63; N, 15.61; Cl, 19.76. Found (corr. for 1.3% $H_2O$): C, 49.89; H, 6.56; N, 15.48; Cl, 19.52.

In a separate experiment, the product obtained after flash chromatography was treated with 20 ml of 3.1N methanolic HCl, then evaporated under reduced pressure and dried to give 5.8 g of the title compound as a trihydrochloride salt.

Anal. Calc'd for $C_{19}H_{27}N_5O_2.3HCl.0.3CH_4O$: C, 48.65; H, 6.60; N, 14.70; Cl, 22.33. Found (corr. for 1.22% $H_2O$): C, 47.54; H, 6.50; N, 14.54; Cl, 21.93.

EXAMPLE 5

5-Nitro-2-{2-[(5-dimethylaminomethyl-3-thienyl)methylthio]ethylamino}-4(3H)-pyrimidone A mixture containing 2-[(5-dimethylaminomethyl-3-thienyl)methylthio]ethylamine (2.88 g; 12.5 mmoles) and 2-methylthio-5-nitro-4-hydroxypyrimidine (2.33 g; 12.44 mmoles) in 10 ml of ethanol was heated at reflux temperature for 13 hours. The reaction mixture was evaporated under reduced pressure, and the residue was placed on 150 g of silica gel and chromatographed by flash chromatography using a gradient elution of methanol-methylene chloride. The appropriate fractions gave 2.92 g of product which was recrystallized from tetrahydrofuran to give the title compound, mp 150°–153° C.

Anal. Calc'd for $C_{14}H_{19}N_5O_3S_2$: C, 45.51; H, 5.18; N, 18.96; S, 17.36. Found: C, 45.87; H, 5.20; N, 19.13; S, 17.45.

EXAMPLE 6

5-Nitro-2-{2-[(5-piperidinomethyl-3-thienyl)methylthio]ethylamino}-4(3H)-pyrimidone A mixture containing 2-[(5-piperidinomethyl-3-thienyl)methylthio]ethylamine (4.85 g; 17.93 mmoles) and 2-methylthio-5-nitro-4-hydroxypyrimidine (3.30 g; 17.62 mmoles) in 15 ml of ethanol was heated at reflux temperature for 18 hours. The reaction mixture was evaporated under reduced pressure and the residue chromatographed on 190 g of silica gel by flash chromatography using a gradient elution of methanol-methylene chloride. The appropriate fractions gave 5.86 g of product which was recrystallized from tetrahydrofuran to give the title compound, mp 144°–145° C. with resolidification and remelting at 193°–194° C.

NMR spectrum (100 MHz) in $d_6$ dimethyl sulfoxide shows the presence of approximately 0.25 moles of tetrahydrofuran.

Anal. Calc'd for $C_{17}H_{25}N_5O_3S_2.0.25C_4H_8O$: C, 50.56; H, 5.89; N, 16.38; S, 15.00. Found: C, 50.80; H, 6.07; N, 15.91; S, 14.68.

EXAMPLE 7

2-{2-[(5-Dimethylaminomethyl-2-furyl)methylthio]ethylamino}-5-nitro-4(3H)-pyrimidone A mixture containing 2-[(5-dimethylaminomethyl-2-furyl)methylthio]ethylamine (4.72 g; 22.0 mmoles) and 2-methylthio-5-nitro-4-hydroxypyrimidine (4.0 g; 21.37 mmoles) in 20 ml of ethanol was heated at reflux temperature for 18 hours. The reaction mixture was evaporated under reduced pressure, and the residue was recrystallized from 2-methoxyethanol to give 5.96 g of the title compound, mp 201°–204° C.

Anal Calc'd for $C_{14}H_{19}N_5O_4S$: C, 47.58; H, 5.42; N, 19.82; S, 9.07. Found: C, 47.22; H, 5.36; N, 19.76; S, 9.06.

EXAMPLE 8

5-Amino-2-{2-[(5-dimethylaminomethyl-3-thienyl)methylthio]ethylamino}-4(3H)-pyrimidone A mixture of 5-nitro-2-{2-[(5-dimethylaminomethyl-3-thienyl)methylthio]ethylamino}-4(3H)-pyrimidone (1.3 g; 3.51 mmoles) and a catalytic amount of Raney nickel No. 28 (approximately 1.4 cm$^3$) in 108 ml of methanol was hydrogenated in a Parr apparatus at 50 psi for 2.5 hours. The reaction mixture was filtered, treated with 1.55N methanolic hydrochloric acid (7.0 ml, 10.9 meq.) and then evaporated under reduced pressure. The residue was placed on 85 g of silica gel and chromatographed by flash chromatography using a gradient elution of methanol:CH$_2$Cl$_2$:H$_2$O from 20:80:1 to 30:70:1. The appropriate fractions were combined and treated with 7.0 ml of 1.55N methanolic HCl, and then evaporated under reduced pressure and dried under high vacuum at 56° C. for 6 hours to give 0.41 g of the title compound as a trihydrochloride salt which had an indeterminate melting point. The NMR spectrum (100 MHz) in d$_6$ dimethyl sulfoxide gave the following resonances δ: 8.88 (m, 6H); 8.18 (m, 1H), 7.82 (s, 1H), 7.56 (s, 1H), 7.40 (s, 1H); 4.50 (s, 2H); 3.82 (s, 2H); 3.50 (m, 2H); 2.73 (m, 8H).

Anal. Calc'd for C$_{14}$H$_{21}$N$_5$OS$_2$.3.5HCl: C, 36.00; H, 5.29; N, 14.99; S, 13.73; Cl, 26.57. Found: C, 36.12; H, 4.77; N, 14.57; S, 13.90; Cl, 25.16.

EXAMPLE 9

5-Amino-2-{2-[(5-piperidinomethyl-3-thienyl)methylthio]ethylamino}-4(3H)-pyrimidone A mixture of 5-nitro-2-{2-[(5-piperidinomethyl-3-thienyl)methylthio]ethylamino}-4(3H)-pyrimidone (5.32 g; 12.96 mmoles) and a catalytic amount of Raney nickel No. 28 (approximately 3.5 cm$^3$) in 300 ml of methanol was hydrogenated in a Parr apparatus at 50 psi for 3.0 hours. The reaction mixture was filtered, treated with 1.55N methanolic HCl (24.0 ml; 37.2 meq.) and evaporated under reduced pressure. The residue was placed on 180 g of silica gel and chromatographed by flash chromatography using a gradient elution of methanol-methylene chloride. The appropriate fractions were combined, evaporated and then rechromatographed using a gradient elution of CH$_3$CN:CH$_3$OH:CH$_2$Cl$_2$ from 7:14:86 to 8:18:80. The appropriate fractions were combined and treated with 20 ml of 1.55N methanolic HCl, and then evaporated under reduced pressure and dried under high vacuum at 56° C. to give 2.35 g of the title compound as a trihydrochloride, mp 150°–155° C.

Anal. Calc'd for C$_{17}$H$_{25}$N$_5$OS$_2$.3.25HCl.0.1CH$_4$O: C, 40.97; H, 5.76; N, 13.97; S, 12.79; Cl, 22.98. Found (corr. for 1.94% H$_2$O): C, 40.77; H, 5.92; N, 14.29; S, 12.52; Cl, 22.80.

EXAMPLE 10

5-Amino-2-{2-[(5-dimethylaminomethyl-2-furyl)methylthio]ethylamino}-4(3H)-pyrimidone To a solution of 2-{2-[(5-dimethylaminomethyl-2-furyl)methylthio]ethylamino}-5-nitro-4(3H)-pyrimidone (4.26 g; 12.05 mmoles) in 50 ml of 2-methoxyethanol containing 1.55N methanolic HCl (7.75 ml; 12.01 meq.) was added a catalytic amount of Raney nickel No. 28 (approximately 2.8 cm$^3$), and the mixture was hydrogenated in a Parr apparatus at 50 psi for 1.25 hours. The reaction mixture was filtered, treated with 20 ml of 1.55N methanolic HCl and evaporated under reduced pressure. The residue was placed on 190 g of silica gel and chromatographed by flash chromatography using CH$_3$OH:CH$_3$CN:NH$_4$OH (20:80:1) as eluent. The appropriate fractions were combined and evaporated to dryness. The residue was dissolved in 25 ml (38.8 meq.) of 1.55N methanolic HCl, evaporated under reduced pressure and dried under high vacuum at 56° C. to give 3.53 g of the title compound as a trihydrochloride, mp 127°–132° C.

Anal. Calc'd for C$_{14}$H$_{21}$N$_5$O$_2$S.3HCl: C, 38.85; H, 5.59; N, 16.18; S, 7.41; Cl, 24.58. Found: C, 38.97; H, 5.59; N, 16.14; S, 7.72; Cl, 23.70.

EXAMPLE 11

5-Formamido-2-[3-(3-piperidinomethylphenoxy)-propylamino]-4(3H)-pyrimidone

To a suspension of 5-amino-2-[3-(3-piperidinomethylphenoxy)propylamino]-4(3H)-pyrimidone trihydrochloride (1.51 g; 3.23 mmoles) [prepared in Example 4] in 10 ml of acetonitrile and 2 ml of methanol was added 6 ml (43.0 mmoles) of triethylamine. The resulting solution was stirred at ambient temperature for 15 minutes and then evaporated under reduced pressure. The residue was dissolved in 10 ml of acetonitrile and treated with phenylformate (2.17 g; 16.0 mmoles). The reaction mixture was evaporated under reduced pressure and the residue was placed on 120 g of silica gel (230–400 mesh) and chromatographed by flash chromatography using a gradient elution of CH$_3$OH:CH$_2$Cl$_2$:NH$_4$OH from 5:95:0.4 to 10:90:0.7. The appropriate fractions were combined and evaporated to give 1.04 g of product. Recrystallization from absolute ethanol yielded the title compound, mp 173°–174° C.

Anal. Calc'd for C$_{20}$H$_{27}$N$_5$O$_3$: C, 62.32; H, 7.06; N, 18.17. Found (corr. for 3.0% H$_2$O): C, 62.19; H, 6.93; N, 18.56.

EXAMPLE 12

The general procedure of Example 3 is repeated and the product thereof is treated by the general procedure of Example 4 except that the 3-(3-piperidinomethylphenoxy)propylamine utilized therein is replaced by an equimolar amount of:

(a) 3-(3-dimethylaminomethylphenoxy)propylamine,
(b) 3-(3-diethylaminomethylphenoxy)propylamine,
(c) 3-(3-pyrrolidinomethylphenoxy)propylamine,
(d) 3-[3-(2-methylpyrrolidino)methylphenoxy]propylamine,
(e) 3-[3-(3-methylpyrrolidino)methylphenoxy]propylamine,
(f) 3-[3-(4-methylpiperidino)methylphenoxy]propylamine,
(g) 3-(3-morpholinomethylphenoxy)propylamine,
(h) 3-[3-(N-methylpiperazino)methylphenoxy]propylamine,
(i) 3-[3-(1,2,3,6-tetrahydro-1-pyridyl)methylphenoxy]propylamine,
(j) 3-(3-hexamethyleneiminomethylphenoxy)propylamine,
(k) 3-(3-heptamethyleneiminomethylphenoxy)propylamine,
(l) 3-[3-(3-azabicyclo[3.2.2]non-3-yl)methylphenoxy]propylamine,
(m) 2-[(5-piperidinomethyl-2-furyl)methylthio]ethylamine,
(n) 2-[(2-guanidinothiazol-4-yl)methylthio]ethylamine,
(o) 2-[(2-dimethylaminomethylthiazol-4-yl)methylthio]ethylamine,
(p) 2-[(5-dimethylaminomethyl-2-thienyl)methylthio]ethylamine,
(q) 2-[(5-pyrrolidinomethyl-3-thienyl)methylthio]ethylamine, (r) 3-(5-dimethylaminomethyl-3-thienyloxy)propylamine,
(s) 3-(5-piperidinomethyl-3-thienyloxy)propylamine,
(t) 2-[(5-dimethylaminomethyl-4-methyl-2-thienyl)methylthio]ethylamine,
(u) 2-[(5-piperidinomethyl-4-methyl-2-thienyl)methylthio]ethylamine,
(v) 3-(3-piperidinomethylthiophenoxy)propylamine,
(w) 2-[(6-dimethylaminomethyl-2-pyridyl)methylthio]ethylamine,
(x) 3-(6-piperidinomethyl-2-pyridyloxy)propylamine,
(y) 3-(6-dimethylaminomethyl-2-pyridyloxy)propylamine,
(z) 2-[(4-dimethylaminomethyl-2-pyridyl)methylthio]ethylamine,
(aa) 2-[(4-piperidinomethyl-2-pyridyl)methylthio]ethylamine,
(bb) 3-(4-dimethylaminomethyl-2-pyridyloxy)propylamine, and
(cc) 3-(4-piperidinomethyl-2-pyridyloxy)propylamine,
and there is thereby produced:
(a) 5-amino-2-[3-(3-dimethylaminomethylphenoxy)-propylamino]-4(3H)-pyrimidone,
(b) 5-amino-2-[3-(3-diethylaminomethylphenoxy)-propylamino]-4(3H)-pyrimidone,
(c) 5-amino-2-[3-(3-pyrrolidinomethylphenoxy)-propylamino]-4(3H)-pyrimidone,
(d) 5-amino-2-{3-[3-(2-methylpyrrolidino)methylphenoxy]propylamino}-4(3H)-pyrimidone
(e) 5-amino-2-{3-[3-(3-methylpyrrolidino)methylphenoxy]propylamino}-4(3H)-pyrimidone,
(f) 5-amino-2-{3-[3-(4-methylpiperidino)methylphenoxy]propylamino}-4(3H)-pyrimidone,
(g) 5-amino-2-[3-(3-morpholinomethylphenoxy)-propylamino]-4(3H)-pyrimidone,
(h) 5-amino-2-{3-[3-(N-methylpiperazino)methylphenoxy]propylamino}-4(3H)-pyrimidone,
(i) 5-amino-2-{3-[3-(1,2,3,6-tetrahydro-1-pyridyl)methylphenoxy]propylamino}-4(3H)-pyrimidone,
(j) 5-amino-2-[3-(3-hexamethyleneiminomethylphenoxy)propylamino]-4(3H)-pyrimidone,
(k) 5-amino-2-[3-(3-heptamethyleneiminomethylphenoxy)propylamino]-4(3H)-pyrimidone,
(l) 5-amino-2-{3-[3-(3-azabicyclo[3.2.2]non-3-yl)methylphenoxy]propylamino}-4(3H)-pyrimidone,
(m) 5-amino-2-{2-[(5-piperidinomethyl-2-furyl)methylthio]ethylamino}-4(3H)-pyrimidone,
(n) 5-amino-2-{2-[(2-guanidinothiazol-4-yl)methylthio]ethylamino}-4(3H)-pyrimidone,
(o) 5-amino-2-{2-[(2-dimethylaminomethylthiazol-4-yl)methylthio]ethylamino}-4(3H)-pyrimidone,
(p) 5-amino-2-{2-[(5-dimethylaminomethyl-2-thienyl)methylthio]ethylamino}-4(3H)-pyrimidone,
(q) 5-amino-2-{2-[(5-pyrrolidinomethyl-3-thienyl)methylthio]ethylamino}-4(3H)-pyrimidone,
(r) 5-amino-2-[3-(5-dimethylaminomethyl-3-thienyloxy)propylamino]-4(3H)-pyrimidone,
(s) 5-amino-2-[3-(5-piperidinomethyl-3-thienyloxy)-propylamino]-4(3H)-pyrimidone,
(t) 5-amino-2-{2-[(5-dimethylaminomethyl-4-methyl-2-thienyl)methylthio]ethylamino}-4(3H)-pyrimidone,
(u) 5-amino-2-{2-[(5-piperidinomethyl-4-methyl-2-thienyl)methylthio]ethylamino}-4(3H)-pyrimidone,
(v) 5-amino-2-[3-(3-piperidinomethylthiophenoxy)-propylamino]-4(3H)-pyrimidone,
(w) 5-amino-2-{2-[(6-dimethylaminomethyl-2-pyridyl)methylthio]ethylamino}-4(3H)-pyrimidone,
(x) 5-amino-2-[3-(6-piperidinomethyl-2-pyridyloxy)-propylamino]-4(3H)-pyrimidone,
(y) 5-amino-2-[3-(6-dimethylaminomethyl-2-pyridyloxy)propylamino]-4(3H)-pyrimidone,
(z) 5-amino-2-{2-[(4-dimethylaminomethyl-2-pyridyl)methylthio]ethylamino}-4(3H)-pyrimidone,
(aa) 5-amino-2-{2-[(4-piperidinomethyl-2-pyridyl)methylthio]ethylamino}-4(3H)-pyrimidone,
(bb) 5-amino-2-[3-(4-dimethylaminomethyl-2-pyridyloxy)propylamino]-4(3H)-pyrimidone, and
(cc) 5-amino2-[3-(4-piperidinomethyl-2-pyridyloxy)-propylamino]-4(3H)-pyrimidone.

What is claimed is:

1. A compound of the formula:

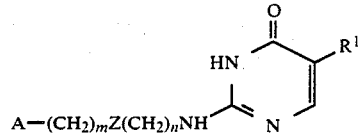

wherein
m is an integer of from zero to 2, inclusive;
n is an integer of from 2 to 5 inclusive;
Z is sulfur, oxygen or methylene;
$R^1$ is $NO_2$ or $NR^2R^3$;
$R^2$ and $R^3$ each are independently hydrogen or (lower)alkyl, or, when $R^2$ is hydrogen, $R^3$ also may be formyl, carboalkoxy, alkanoyl or benzoyl;
A is phenyl, furyl, thienyl, pyridyl, thiazolyl, imidazolyl, oxazolyl, or pyrimidinyl; provided that A has one or two substituents, the first substituent being selected from

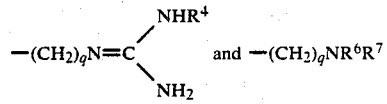

and the second substituent being selected from (lower)alkyl, hydroxy, trifluoromethyl, halogen, hydroxymethyl and (lower)alkoxy, and provided that A is attached solely via its carbon atoms;
q is an integer of from 0 to 6, inclusive;
$R^4$ is a hydrogen atom, a (lower)alkyl group optionally substituted by one or more halogen atoms selected from fluorine, bromine and chlorine, provided that there is no halogen atom on the carbon atom attached to the nitrogen atom, or a cyclo(lower)alkyl, cyclo(lower)alkyl(lower)alkyl, (lower)alkanoyl or benzoyl group;
$R^6$ and $R^7$ are each independently hydrogen, (lower)alkyl, (lower)alkenyl, (lower)alkynyl, phenyl(lower)alkyl or (lower)alkoxy(lower)alkyl in which the (lower)alkoxy moiety is at least two carbon atoms removed from the nitrogen atom, or $R^6$ and $R^7$, taken together with the nitrogen atom to which they are attached, may be pyrrolidino, methylpyrrolidino, dimethylpyrrolidino, morpholino, thiomorpholino, piperidino, methylpiperidino, dimethylpiperidino, hydroxypiperidino, N-methylpiperazino, homopiperidino, heptamethyleneimino, octamethyleneimino or 3-azabicyclo[3.2.2]non-3-yl; or a nontoxic pharmaceutically acceptable acid addition salt thereof.

2. A compound of claim 1 wherein $R^1$ is $NO_2$, $NH_2$, $NHCO_2C_2H_5$, or NHCHO; substituent A is piperidinomethylphenyl, dimethylaminomethylthienyl, piperidinomethylthienyl, or dimethylaminomethylfuryl; substituent $R^4$ is hydrogen, (lower)alkyl or 2,2,2-trifluoroethyl substituent Z is sulfur or oxygen; m is zero or 1; and n is 2 or 3.

3. The compound of claim 1 which is 5-carbethoxyamino-2-[3-(3-piperidinomethylphenoxy)-propylamino]-4(3)-pyrimidone and nontoxic pharmaceutically acceptable acid addition salts thereof.

4. The compound of claim 1 which is 5-amino-2-[3-(3-piperidinomethylphenoxy)propylamino]-4-(3H)-pyrimidone and nontoxic pharmaceutically acceptable acid addition salts thereof.

5. The compound of claim 1 which is 5-nitro-2-[3-(3-piperidinomethylphenoxy)propylamino]-4(3H)-pyrimidone and nontoxic pharmaceutically acceptable acid addition salts thereof.

6. The compound of claim 1 which is 5-nitro-2-{2-[(5-dimethylaminomethyl-3-thienyl)methylthio]ethylamino}-4(3H)-pyrimidone and nontoxic pharmaceutically acceptable acid addition salts thereof.

7. The compound of claim 1 which is 5-nitro-2-}2-[(5-piperidinomethyl-3-thienyl)methylthio]ethylamino}-4(3H)-pyrimidone and nontoxic pharmaceutically acceptable acid addition salts thereof.

8. The compound of claim 1 which is 2-{2-[(5-dimethylaminomethyl-2-furyl)methylthio]ethylamino}-5-nitro-4(3)-pyrimidone and nontoxic pharmaceutically acceptable acid addition salts thereof.

9. The compound of claim 1 which is 5-amino-2-{2-[(5-dimethylaminomethyl-3-thienyl)methylthio]ethylamino}-4(3H)-pyrimidone and nontoxic pharmaceutically acceptable acid addition salts thereof.

10. The compound of claim 1 which is 5-amino-2-{2-[(5-piperidinomethyl-3-thienyl)methylthio]ethylamino}-4(3H)-pyrimidone and nontoxic pharmaceutically acceptable acid addition salts thereof.

11. The compound of claim 1 which is 5-amino-2-{2-[(5-dimethylaminomethyl-2-furyl)methylthio]ethylamino}-4(3H)-pyrimidone and nontoxic pharmaceutically acceptable acid addition salts thereof.

12. The compound of claim 1 which is 5-formamido-2-[3-(3-piperidinomethylphenoxy)propylamino]-4(3H)-pyrimidone and nontoxic pharmaceutically acceptable acid addition salts thereof.

13. A compound selected from the group consisting of 5-($C_1$-$C_6$)alkanoylamido-2-(3-(3-piperidino methyl phenoxy)-propylamino)-4(3H)-pyrimidone,5-amino-2-(3-(3-piperidinomethyl phenoxy)-propylamino-4(3H)-pyrimidone and nontoxic pharmaceutically acceptable acid addition salts thereof.

14. A compound selected from the group consisting of 5-($C_1$-$C_6$)alkanoylamino-2-(3-(3-piperidinomethylphenoxyl)propylamino)-4(3H)-pyrimidone,5-amino-2-(3-(3-piperidinomethylphenoxy)propylamino)-4(3H)-pyrimidone and nontoxic pharmaceutically acceptable acid addition salts thereof.

15. A compound selected from the group consisting of 5-($C_1$-$C_6$)alkanoylamino-2-(3-(3-piperidinomethylphenoxy)propylamino)-4 (3H)-pyrimidone,5-amino-2-(3-(3-piperidinomethylphenoxy)propylamino)-4(3H)-pyrimidone,5-($C_1$-$C_6$)alkoxycarbonylamino-2-(3-(3-piperidinomethylphenoxy)-propylamino)-4(3H)pyrimidone and nontoxic pharmaceutically acceptable acid addition salts thereof.

16. A compound of the formula:

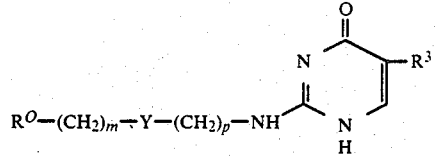

wherein
$R^3$ is $NO_2$ or $NHR^4$;
$R^4$ is hydrogen, $C_{1-6}$ alkanoyl or $C_{1-6}$ alkoxy carbonyl;
P is 2, 3, or 4;
Y is oxygen, sulfur or methylene;
m is 1; or if Z if pyridyl or phenylene, m may also be zero;
$R^0$ is 2-guanidinothiazol-4-yl or a group $R^1R^2N(CH_2)_n$—Z—; wherein;
$R^1$ and $R^2$ are independently hydrogen, $C_{1-6}$ alkyl, hydroxy($C_{2-6}$)alkyl, phenyl($C_{1-6}$)alkyl; or
$R^1$ and $R^2$ together represent —$(CH_2)_g$—wherein
g is 4 to 7, to form together with the nitrogen atom to which they are attached a 5-8 membered saturated ring;
n is an integer from 1 to 6;
Z is 2,5-furanyl, 2,5-thienyl, 2,4-pyridyl wherein the $R^1R^2N(CH_2)_n$ is in the 4-position, 2,4-thiazolyl wherein the $R^1R^2N(CH_2)_n$ group is in the 2-position, or 1,3- or 1,4-phenylene;
or a pharmaceutically acceptable salt thereof.

* * * * *